(12) United States Patent
Lee et al.

(10) Patent No.: US 8,906,101 B2
(45) Date of Patent: Dec. 9, 2014

(54) INTERBODY VERTEBRAL PROSTHETIC AND ORTHOPEDIC FUSION DEVICE WITH SELF-DEPLOYING ANCHORS

(71) Applicant: Amicus Design Group, LLC, Grand Prairie, TX (US)

(72) Inventors: Randall F. Lee, Grand Prairie, TX (US); Daniel S. Savage, Cleveland, OH (US); Alan W. Rorke, Bristol (GB); Richard D. Guyer, Plano, TX (US); Jack E. Zigler, Plano, TX (US)

(73) Assignee: Amicus Design Group, LLC, Grand Prairie, TX (US)

( * ) Notice: Subject to any disclaimer, the term of this patent is extended or adjusted under 35 U.S.C. 154(b) by 0 days.

(21) Appl. No.: 14/176,714

(22) Filed: Feb. 10, 2014

(65) Prior Publication Data

US 2014/0156010 A1    Jun. 5, 2014

Related U.S. Application Data

(62) Division of application No. 13/770,511, filed on Feb. 19, 2013, now Pat. No. 8,685,104.

(60) Provisional application No. 61/612,423, filed on Mar. 19, 2012, provisional application No. 61/756,707, filed on Jan. 25, 2013.

(51) Int. Cl.
*A61F 2/44*    (2006.01)
*A61F 2/46*    (2006.01)
*A61F 2/30*    (2006.01)

(52) U.S. Cl.
CPC ............... *A61F 2/4611* (2013.01); *A61F 2/447* (2013.01); *A61F 2/4465* (2013.01); *A61F 2/442* (2013.01); *A61F 2002/30378* (2013.01); *A61F 2002/30507* (2013.01); *A61F 2002/30579* (2013.01); *A61F 2002/30604* (2013.01)
USPC .................... 623/17.16; 623/17.11; 623/17.14

(58) Field of Classification Search
CPC ....... A61F 2/44; A61F 2/4455; A61F 2/4465; A61F 2/447; A61F 2220/0008; A61F 2220/0016; A61F 2/4611; A61F 2002/30579
USPC ............................................ 623/17.11–17.16
See application file for complete search history.

(56) References Cited

U.S. PATENT DOCUMENTS 4,863,476 A    9/1989    Shepperd
4,904,261 A    2/1990    Dove et al.
(Continued)

FOREIGN PATENT DOCUMENTS

EP    0697500 A1    2/1996
FR    835179 A1    8/2003
(Continued)

OTHER PUBLICATIONS

International Search Report and Written Opinion for corresponding PCT application No. PCT/US2009/060602, Jan. 11, 2010.

(Continued)

*Primary Examiner* — Eduardo C Robert
*Assistant Examiner* — Julianna N Harvey
(74) *Attorney, Agent, or Firm* — Matthew B. Dernier, Esq.; Gibson & Dernier LLP

(57) ABSTRACT

A method of inserting an intervertebral prosthesis into an intervertebral space between respective endplates of adjacent first and second vertebral bones of a spine, includes: placing the intervertebral prosthesis into the intervertebral space, the intervertebral prosthesis including: a body including first and second spaced apart major surfaces and at least one sidewall extending therebetween, the first major surface for engaging the endplate of the first vertebral bone, and the second major surface for engaging the endplate of the second vertebral bone, and the first and second major surfaces defining a longitudinal axis extending substantially normal to said surfaces; and simultaneously pushing at least three anchoring elements from within the body of the intervertebral prosthesis out through at least three respective apertures in the body and into at least one of the first and second vertebral bones, without rotating the at least one anchoring element about an axis thereof.

11 Claims, 10 Drawing Sheets

(56) References Cited

U.S. PATENT DOCUMENTS

| | | |
|---|---|---|
| 4,955,908 A | 9/1990 | Frey et al. |
| 5,387,218 A | 2/1995 | Meswania |
| 5,397,364 A | 3/1995 | Kozak et al. |
| 5,522,899 A | 6/1996 | Michelson |
| 5,571,109 A | 11/1996 | Bertagnoli |
| 5,609,635 A | 3/1997 | Michelson |
| 5,658,335 A | 8/1997 | Allen |
| 5,800,547 A | 9/1998 | Schaefer |
| 5,800,550 A | 9/1998 | Sertich |
| 5,888,223 A | 3/1999 | Bray, Jr. |
| 5,976,139 A | 11/1999 | Bramlet |
| 6,022,363 A | 2/2000 | Walker et al. |
| 6,066,175 A | 5/2000 | Henderson et al. |
| 6,077,264 A | 6/2000 | Chemello |
| 6,096,080 A | 8/2000 | Nicholson et al. |
| 6,113,638 A | 9/2000 | Williams et al. |
| 6,156,037 A | 12/2000 | LeHuec et al. |
| 6,179,873 B1 | 1/2001 | Zientek |
| 6,183,474 B1 | 2/2001 | Bramlet et al. |
| 6,190,414 B1 | 2/2001 | Young et al. |
| 6,193,757 B1 | 2/2001 | Foley |
| 6,235,059 B1 | 5/2001 | Benezech et al. |
| 6,241,769 B1 | 6/2001 | Nicholson et al. |
| 6,306,170 B2 | 10/2001 | Ray |
| 6,432,106 B1 | 8/2002 | Fraser |
| 6,443,954 B1 | 9/2002 | Bramlet et al. |
| 6,447,546 B1 | 9/2002 | Bramlet et al. |
| 6,461,359 B1 | 10/2002 | Tribus et al. |
| 6,471,724 B2 | 10/2002 | Zdeblick et al. |
| 6,527,803 B1 * | 3/2003 | Crozet et al. ............... 623/17.11 |
| 6,558,423 B1 | 5/2003 | Michelson |
| 6,572,619 B2 | 6/2003 | Santilli |
| 6,579,290 B1 | 6/2003 | Hardcastle et al. |
| 6,695,851 B2 | 2/2004 | Zdeblick et al. |
| 6,716,245 B2 | 4/2004 | Pasquet et al. |
| 6,743,256 B2 | 6/2004 | Mason |
| 6,749,636 B2 | 6/2004 | Michelson |
| 6,752,832 B2 | 6/2004 | Neumann |
| 6,770,096 B2 * | 8/2004 | Bolger et al. ............... 623/17.16 |
| 6,800,092 B1 | 10/2004 | Williams et al. |
| 6,800,093 B2 | 10/2004 | Nicholson et al. |
| 6,805,714 B2 | 10/2004 | Sutcliffe |
| 6,890,355 B2 | 5/2005 | Michelson |
| 6,899,735 B2 | 5/2005 | Coates et al. |
| 6,972,019 B2 | 12/2005 | Michelson |
| 6,984,234 B2 | 1/2006 | Bray |
| 7,018,414 B2 | 3/2006 | Brau et al. |
| 7,018,415 B1 | 3/2006 | McKay |
| 7,041,135 B2 | 5/2006 | Michelson |
| 7,077,864 B2 | 7/2006 | Byrd, III et al. |
| 7,135,024 B2 | 11/2006 | Cook et al. |
| 7,163,560 B2 | 1/2007 | Mason |
| 7,163,561 B2 | 1/2007 | Michelson |
| 7,166,110 B2 | 1/2007 | Yundt |
| 7,172,627 B2 | 2/2007 | Fiere et al. |
| 7,232,464 B2 | 6/2007 | Mathieu et al. |
| 7,291,170 B2 | 11/2007 | Huppert |
| 7,297,162 B2 | 11/2007 | Mujwid |
| 8,062,374 B2 | 11/2011 | Markworth |
| 8,343,219 B2 | 1/2013 | Allain |
| 2002/0049444 A1 | 4/2002 | Knox |
| 2002/0143399 A1 | 10/2002 | Sutcliffe |
| 2003/0014113 A1 | 1/2003 | Ralph et al. |
| 2003/0014114 A1 | 1/2003 | Ralph et al. |
| 2003/0014115 A1 | 1/2003 | Ralph et al. |
| 2003/0014116 A1 | 1/2003 | Ralph et al. |
| 2003/0023309 A1 | 1/2003 | Ralph et al. |
| 2003/0023310 A1 | 1/2003 | Ralph et al. |
| 2003/0025408 A1 | 2/2003 | Miekka et al. |
| 2003/0028252 A1 | 2/2003 | Ralph et al. |
| 2003/0073998 A1 | 4/2003 | Pagliuca et al. |
| 2003/0074075 A1 | 4/2003 | Thomas, Jr. et al. |
| 2003/0125739 A1 | 7/2003 | Bagga et al. |
| 2003/0187436 A1 | 10/2003 | Bolger et al. |
| 2003/0199983 A1 | 10/2003 | Michelson |
| 2003/0233147 A1 | 12/2003 | Nicholson |
| 2004/0002764 A1 | 1/2004 | Gainor et al. |
| 2004/0020568 A1 | 2/2004 | Phelps et al. |
| 2004/0024463 A1 | 2/2004 | Thomas, Jr. et al. |
| 2004/0039384 A1 | 2/2004 | Boehm, Jr. et al. |
| 2004/0093089 A1 | 5/2004 | Ralph et al. |
| 2004/0097924 A1 | 5/2004 | Lambrecht et al. |
| 2004/0133201 A1 | 7/2004 | Shluzas et al. |
| 2004/0153075 A1 | 8/2004 | Roger |
| 2004/0158326 A1 | 8/2004 | Ralph et al. |
| 2004/0176853 A1 | 9/2004 | Sennett et al. |
| 2004/0199254 A1 | 10/2004 | Louis |
| 2004/0249466 A1 | 12/2004 | Liu et al. |
| 2005/0013832 A1 | 1/2005 | Rose |
| 2005/0013833 A1 | 1/2005 | Simonnet |
| 2005/0021030 A1 | 1/2005 | Pagliuca et al. |
| 2005/0033297 A1 | 2/2005 | Davison |
| 2005/0033299 A1 | 2/2005 | Shluzas |
| 2005/0043798 A1 | 2/2005 | Eckman |
| 2005/0049590 A1 | 3/2005 | Alleyne |
| 2005/0055027 A1 | 3/2005 | Yeung et al. |
| 2005/0090822 A1 | 4/2005 | DiPoto |
| 2005/0131543 A1 | 6/2005 | Benzel et al. |
| 2005/0159819 A1 | 7/2005 | McCormack et al. |
| 2005/0261684 A1 | 11/2005 | Shaolian et al. |
| 2005/0273173 A1 | 12/2005 | Gordon et al. |
| 2005/0273174 A1 | 12/2005 | Gordon et al. |
| 2005/0273175 A1 | 12/2005 | Gordon et al. |
| 2005/0283245 A1 | 12/2005 | Gordon et al. |
| 2005/0283247 A1 | 12/2005 | Gordon et al. |
| 2005/0283248 A1 | 12/2005 | Gordon et al. |
| 2006/0024162 A1 | 2/2006 | Giffin |
| 2006/0030851 A1 | 2/2006 | Bray et al. |
| 2006/0047342 A1 | 3/2006 | Khoshnevis |
| 2006/0058800 A1 | 3/2006 | Ainsworth et al. |
| 2006/0079898 A1 | 4/2006 | Ainsworth et al. |
| 2006/0095136 A1 | 5/2006 | McLuen |
| 2006/0142859 A1 | 6/2006 | McLuen |
| 2006/0155379 A1 | 7/2006 | Heneveld, Sr. et al. |
| 2006/0173543 A1 | 8/2006 | Brau et al. |
| 2006/0195092 A1 | 8/2006 | Barry |
| 2006/0200239 A1 | 9/2006 | Rothman et al. |
| 2006/0206208 A1 | 9/2006 | Michelson |
| 2006/0229729 A1 | 10/2006 | Gordon et al. |
| 2006/0235391 A1 | 10/2006 | Sutterlin, III |
| 2006/0241621 A1 | 10/2006 | Moskowitz et al. |
| 2006/0247643 A1 | 11/2006 | Bhatnagar et al. |
| 2006/0247644 A1 | 11/2006 | Bhatnagar et al. |
| 2006/0247784 A1 | 11/2006 | Kim |
| 2006/0253132 A1 | 11/2006 | Evans et al. |
| 2006/0253201 A1 | 11/2006 | McLuen |
| 2006/0276790 A1 | 12/2006 | Dawson et al. |
| 2006/0276897 A1 | 12/2006 | Winslow |
| 2006/0287731 A1 | 12/2006 | Cauthen, III et al. |
| 2007/0005140 A1 | 1/2007 | Kim et al. |
| 2007/0010816 A1 | 1/2007 | Wilkinson et al. |
| 2007/0010821 A1 | 1/2007 | Wilkinson et al. |
| 2007/0021750 A1 | 1/2007 | Shluzas et al. |
| 2007/0038222 A1 | 2/2007 | Bhatnagar et al. |
| 2007/0043361 A1 | 2/2007 | Malandain et al. |
| 2007/0043362 A1 | 2/2007 | Malandain et al. |
| 2007/0043363 A1 | 2/2007 | Malandain et al. |
| 2007/0049943 A1 | 3/2007 | Moskowitz et al. |
| 2007/0049944 A1 | 3/2007 | Stone et al. |
| 2007/0055379 A1 | 3/2007 | Stone et al. |
| 2007/0078460 A1 | 4/2007 | Frigg et al. |
| 2007/0093827 A1 | 4/2007 | Warnick |
| 2007/0100348 A1 | 5/2007 | Cauthen, III et al. |
| 2007/0100452 A1 | 5/2007 | Prosser |
| 2007/0106384 A1 | 5/2007 | Bray et al. |
| 2007/0106388 A1 | 5/2007 | Michelson |
| 2007/0112351 A1 | 5/2007 | Assell et al. |
| 2007/0156245 A1 | 7/2007 | Cauthen, III et al. |
| 2007/0162129 A1 | 7/2007 | Edie et al. |
| 2007/0162139 A1 | 7/2007 | Ralph et al. |
| 2007/0168043 A1 | 7/2007 | Ferree |
| 2007/0179623 A1 | 8/2007 | Trieu et al. |
| 2007/0198021 A1 | 8/2007 | Wales |
| 2007/0219634 A1 | 9/2007 | Greenhalgh et al. |

(56) References Cited

U.S. PATENT DOCUMENTS

| | | |
|---|---|---|
| 2007/0233083 A1 | 10/2007 | Abdou |
| 2007/0233253 A1 | 10/2007 | Bray et al. |
| 2007/0239159 A1 | 10/2007 | Altarac et al. |
| 2007/0239160 A1 | 10/2007 | Zipnick et al. |
| 2007/0250167 A1 | 10/2007 | Bray et al. |
| 2007/0260245 A1 | 11/2007 | Malandain et al. |
| 2007/0265623 A1 | 11/2007 | Malandain et al. |
| 2007/0270842 A1 | 11/2007 | Bankoski et al. |
| 2007/0270960 A1 | 11/2007 | Bonin, Jr. et al. |
| 2007/0276370 A1 | 11/2007 | Altarac et al. |
| 2007/0276372 A1 | 11/2007 | Malandain et al. |
| 2007/0276373 A1 | 11/2007 | Malandain |
| 2007/0276377 A1 | 11/2007 | Yundt |
| 2007/0293948 A1 | 12/2007 | Bagga et al. |
| 2008/0009826 A1 | 1/2008 | Miller et al. |
| 2008/0009828 A1 | 1/2008 | Miller et al. |
| 2008/0009880 A1 | 1/2008 | Warnick et al. |
| 2008/0009944 A1 | 1/2008 | McGuckin, Jr. |
| 2008/0018660 A1 | 1/2008 | Nenonen et al. |
| 2008/0021687 A1 | 1/2008 | Hunter et al. |
| 2008/0021692 A1 | 1/2008 | Chaudhry et al. |
| 2008/0027449 A1 | 1/2008 | Gundlapalli et al. |
| 2008/0027550 A1 | 1/2008 | Link et al. |
| 2008/0033558 A1 | 2/2008 | Zucherman et al. |
| 2008/0033559 A1 | 2/2008 | Zucherman et al. |
| 2008/0033560 A1 | 2/2008 | Zucherman et al. |
| 2008/0039846 A1 | 2/2008 | Lee et al. |
| 2008/0039947 A1 | 2/2008 | Zucherman et al. |
| 2008/0046081 A1 | 2/2008 | Zucherman et al. |
| 2008/0051898 A1 | 2/2008 | Zucherman et al. |
| 2008/0051899 A1 | 2/2008 | Zucherman et al. |
| 2008/0058935 A1 | 3/2008 | Malandain et al. |
| 2008/0071274 A1 | 3/2008 | Ensign |
| 2008/0071376 A1 | 3/2008 | Kohm et al. |
| 2008/0077136 A1 | 3/2008 | Triplett et al. |
| 2008/0082170 A1 | 4/2008 | Peterman |
| 2008/0108990 A1 | 5/2008 | Mitchell et al. |
| 2008/0109005 A1 | 5/2008 | Trudeau et al. |
| 2008/0114454 A1 | 5/2008 | Peterman et al. |
| 2008/0119935 A1 | 5/2008 | Alvarez |
| 2008/0140207 A1 | 6/2008 | Olmos et al. |
| 2008/0147192 A1 | 6/2008 | Edidin et al. |
| 2008/0147194 A1 | 6/2008 | Grotz et al. |
| 2008/0154382 A1 | 6/2008 | de Villiers et al. |
| 2008/0161933 A1 | 7/2008 | Grotz et al. |
| 2008/0167686 A1 | 7/2008 | Trieu et al. |
| 2008/0167718 A1 | 7/2008 | Protopsaltis |
| 2008/0177306 A1 | 7/2008 | Lamborne et al. |
| 2008/0221694 A1 | 9/2008 | Warnick et al. |
| 2008/0275455 A1 | 11/2008 | Berry et al. |
| 2008/0275456 A1 | 11/2008 | Vonwiller et al. |
| 2008/0281424 A1 | 11/2008 | Parry et al. |
| 2008/0288075 A1 | 11/2008 | Zucherman et al. |
| 2008/0292161 A1 | 11/2008 | Funk et al. |
| 2008/0294263 A1 | 11/2008 | Altarac et al. |
| 2009/0012528 A1 | 1/2009 | Aschmann et al. |
| 2009/0018660 A1 | 1/2009 | Roush |
| 2009/0030522 A1 | 1/2009 | Cauthen, III et al. |
| 2009/0036937 A1 | 2/2009 | Cauthen, III et al. |
| 2009/0036989 A1 | 2/2009 | Cauthen, III et al. |
| 2009/0036990 A1 | 2/2009 | Cauthen, III et al. |
| 2009/0043343 A1 | 2/2009 | Wales |
| 2009/0043394 A1 | 2/2009 | Zdeblick et al. |
| 2009/0054988 A1 | 2/2009 | Hess |
| 2009/0105832 A1 | 4/2009 | Allain et al. |
| 2009/0164020 A1 | 6/2009 | Janowski |
| 2009/0265007 A1 | 10/2009 | Colleran |
| 2009/0292316 A1 | 11/2009 | Hess |
| 2010/0100100 A1 | 4/2010 | Refai |
| 2010/0137989 A1 | 6/2010 | Armstrong |
| 2010/0160984 A1 | 6/2010 | Berry |
| 2010/0161057 A1 | 6/2010 | Berry |
| 2010/0185289 A1 | 7/2010 | Kirwan et al. |
| 2010/0262247 A1 | 10/2010 | Arnin |
| 2011/0035007 A1* | 2/2011 | Patel et al. ................. 623/17.11 |
| 2011/0230971 A1 | 9/2011 | Donner et al. |
| 2012/0078371 A1 | 3/2012 | Gamache et al. |

FOREIGN PATENT DOCUMENTS

| | | |
|---|---|---|
| WO | 9966867 A1 | 12/1999 |
| WO | 2004078218 A2 | 9/2004 |
| WO | 2004080356 A2 | 9/2004 |
| WO | 2008149223 | 12/2008 |
| WO | 2010121028 A2 | 10/2010 |

OTHER PUBLICATIONS

International Search Report and Written Opinion for corresponding PCT application No. PCT/US2013/026689, May 8, 2013.

Promotional material for SynFix™ (www.synthes.com). (published at least as early as Jun. 2008).

Promotional material for VerteBridge™ (www.ldrholding.com) (published at least as early as Jun. 2008).

Promotional material for Stalif TM (published at least as early as Jun. 2008).

International Preliminary Report on Patentability and Written Opinion for related application PCT/US2013/026689, dated Oct. 2, 2014.

* cited by examiner

100

100

100

100C

INTERBODY VERTEBRAL PROSTHETIC AND ORTHOPEDIC FUSION DEVICE WITH SELF-DEPLOYING ANCHORS

CROSS REFERENCE TO RELATED APPLICATIONS

This application is a divisional of U.S. Non-provisional patent application Ser. No. 13/770,511, filed Feb. 19, 2013, which claims the benefit of U.S. Provisional Patent Application No. 61/612,423, filed Mar. 19, 2012, and U.S. Provisional Patent Application No. 61/756,707, filed Jan. 25, 2013, the entire disclosures of which are hereby incorporated by reference.

BACKGROUND

The present disclosure generally relates to apparatus and methods for treatment of spinal disorders using an intervertebral prosthesis which is disposed in an intervertebral space (or cavity) following removal of a damaged or diseased intervertebral disc. However the varied orthopedic embodiments of this apparatus and the methods used therein constitute the basic concept of the invention of fusion cages implanted throughout the human skeleton.

The bones and connective tissue of an adult human spinal column consist of more than thirty three discrete bones coupled sequentially to one another by a tri-joint complex. Each tri-joint complex includes an anterior disc and two posterior facet joints. The anterior space between adjacent bones are cushioned by collagen spacers referred to as intervertebral discs. The spine nomenclature of these bones are anatomically categorized as being members of one of four classifications: cervical, thoracic, lumbar, or sacral. The cervical portion of the spine, which comprises the top of the spine, up to the base of the skull, includes the first seven vertebrae. The intermediate twelve bones are the thoracic vertebrae, and connect to the lower spine comprising the five lumbar vertebrae. The base of the spine includes the sacral bones (including the coccyx). The component bones of the cervical spine are generally smaller than those of the thoracic spine, which are in turn smaller than those of the lumbar region. The sacral region connects to the pelvis.

The spinal column is highly complex in that it includes all these bones and viscoelastic structures coupled to one another, housing and protecting critical elements of the nervous system having innumerable peripheral nerves and circulatory bodies in close proximity. In spite of these conditions, the spine is a highly flexible structure, capable of a high degree of curvature and twist in nearly every direction.

Genetic or developmental irregularities, trauma, chronic stress, tumors, and degenerative wear are a few of the factors that can result in spinal pathologies for which surgical intervention may be necessary. A variety of systems have been disclosed in the art that achieve immobilization and/or fusion of adjacent bones by implanting artificial assemblies in or on the spinal column. The region of the back that needs to be immobilized, as well as the individual variations in anatomy, determines the appropriate surgical protocol and implantation assembly. The spine surgical community has accepted intervertebral devices (commonly known as interbody spacers, and allograft transplants) as part of the state of the art and routinely employ such devices in the reconstruction of collapsed inter-vertebral disc spaces.

Surgeons insert these intervertebral devices to adjunctively facilitate bone fusion in between and into the contiguous involved vertebrae. This fusion creates a new solid bone mass, which acts to hold the spinal segment at an appropriate biomechanically restored height as well as to stop motion in a segment of the spine in which the patient is experiencing pain. Items surgically placed in these involved interbody regions can thus stimulate interbody bone in-growth such that the operated anterior spinal segments heal into a contiguous bone mass; in other words, a fusion occurs. Further, the surgical community uses such man-made implants or biological options to provide weight bearing support between adjacent vertebral bodies, and thereby correct or alleviate a variety of mechanically related clinical problems. In this regard, surgeons use intervertebral spinal implants/transplants for surgical therapy for degenerative disc disease (DDD), discogenic low back pain, spondylolisthesis, reconstruction following tumor or infection surgery, and other spine related maladies requiring surgical intervention.

In many implant designs, a relatively hard or sturdy implant construct is formed from a selected biocompatible material such as metal, ceramic, plastic, or carbon fiber-reinforced polymer. This implant construct often has a partially open or porous configuration and is coated or partially filled with a selected bone ingrowth-enhancing substance, such as harvested bone graft supplied from the patient, human donor allograft bone transplant material supplied by a tissue bank, genetically cultivated bone growing protein substitutes, and/or other biological/biochemical bone extenders. Such devices, when implanted into the intervertebral space, promote ingrowth of blood supply and grow active and live bone from the adjacent spinal vertebrae to inter-knit with the implant, thereby eventually immobilizing or fusing the adjacent spinal vertebrae. Such implants also commonly include a patterned exterior surface such as a ribbed or serrated surface, or screw thread geometry, to achieve enhanced mechanical locking with the adjacent vertebrae during the bone ingrowth/fusion process.

With respect to the failure of the intervertebral disc, the interbody fusion cage has generated substantial interest because it can be implanted into the anterior aspect of the spine. Cylindrical intervertebral discal cages generally comprise a tubular metal body having an external surface threading. They are inserted transverse to the axis of the spine, into preformed cylindrical holes at the junction of adjacent vertebral bodies. The cages include holes through which the adjacent bones are to grow. Additional materials, for example autogenous bone graft materials, may be inserted into the hollow interior of the cage to incite or accelerate the growth of the bone into the cage.

Conventional intervertebral discal cages generally comprises a device with a geometry that mimics the shape of the intervertebral disc, made of plastic, carbon fiber, metal, or human tissue, having an upper and lower surface which are designed to interface with well prepared flat vertebral body endplate structures. These cages are designed to interface transversely to the axis of the spine into completely shelled out disc spaces, the geometry of the cage mirroring the hollow intervertebral disc space. The cages include at least one large graft hole in line with the spinal axis through which the superior and inferior endplates may form an osseous column and fuse. Typically, these holes are packed with a variety of graft, graft enhancing, bone generating, or bone substitute like materials.

Additionally, the spine surgery community has generated several commercially available cages with integrated screws that operate as stand-alone support devices (that is, without supplemental support from an additional construct such as an anterior plate and screws, or posteriorly placed transpedicular screws and rods or screws placed through the facet joints)

interbody fusion devices. These devices include the Stalif™, SynFix™, and the VerteBridge™. The Stalif™ is a device for the fusion of the lumbar spine. The implant is inserted and fixed via converging screws passing through pre-drilled apertures of the device that penetrate into the vertebral bodies. The screws are manually placed into the apertures of the device and are driven using an appropriate tool, such as a surgical screw driver. The Stalif™ is available from Centinel Spine, www.centinelspine.com. The SynFix™ is also a device that is placed in an intervertebral space and fixed via diverging screws passing through the device and into the vertebral bodies. Again, the screws are manually placed into the apertures of the device and are driven using a surgical screw driver. The SynFix™ is available from Synthes, Inc., 1302 Wrights Lane East, West Chester, Pa. 19380 (www.synthes.com). The VerteBridge™ is a device for the fusion of the spine in which anchoring blades are press-driven (using a specialized tool) through apertures in the device and into the respective vertebral bodies to fix the device in place. The VerteBridge™ is available through the LDR Spine (www.ldrholding.com).

All of the above-described devices have an anchor which is secondarily added to the initial device. The Stalif™ and SynFix™ devices employ screws while the VerteBridge™ utilizes a blade anchor. Both the Stalif™ and SynFix™ devices require the screws to be inserted at trajectories that are difficult to achieve given common human anatomical structures, especially at the spinal disc space levels of L4-L5-S1. Additionally, the proximal end of the screws may protrude anteriorly, causing potential irritation and erosion to the great and small vessels, and possibly through innocent misadventure snag ureters and surrounding soft tissue as the screw is blindly approximated and then secured into its home/locked position.

The VerteBridge™ has a pair of blades inserted after the initial device is put in place. The blades are supposed to flex enough to curve within the device, and to exhibit sufficient strength to cut through bone. These blades, although flexible, need to be able to hold the vertebral bodies in place in all planes of motion under normal physiologic and, to a degree, superphysiologic conditions. In practice, these features may not always be achieved.

A number of devices have been developed, which employ self-contained anchoring elements that are deployed after the device is placed into the intervertebral space. For example, U.S. Patent Application Pub. No. 2006/0241621 (incorporated herein in its entirety) discloses a device for joining intervertebral members together using a self-drilling screw apparatus. The screw apparatus includes a shell and first and second screw members having tapered ends and threaded bodies that are disposed within the shell. A drive mechanism rotationally drives the first and second screw members from the shell in precisely co-axial, opposite directions, which causes the screw members to embed themselves in the vertebral bodies. U.S. Pat. No. 5,800,550 (incorporated herein in its entirety) discloses a device for joining intervertebral members together using a self-deploying pair of posts. The apparatus includes a body and first and second post members that are disposed within the body. A drive mechanism press-drives the first and second posts from the body in precisely co-axial, opposite directions (longitudinally aligned with the spine), which causes the posts to embed themselves in the vertebral bodies. The problems with these devices include that the co-axial, opposite deployment of the screws/posts is not an ideal configuration for fixing an intervertebral device. Indeed, such a deployment may permit slippage of the device during or after deployment because of the natural stresses applied to the device from the patient's anatomical spinal structures.

Another approach is disclosed in U.S. 2010/0161057, the entire disclosure of which is incorporated herein in its entirety. That publication discloses an intervertebral prosthesis that includes a body having one or more apertures extending transversely therefrom with respect to the longitudinal axis. Respective anchoring elements disposed within the apertures are threaded and deploy in response to a driving rotational force on a gear. The gear is disposed adjacent to, and in meshed threaded communication with, the threaded shaft of the anchoring elements such that rotation of the gear causes rotational torque of the anchoring elements. The driving rotational force on the gear causes the anchoring elements to rotate, deploy from the body, and thread into the vertebral bone of the patient's spine.

Despite the advancements in the art, there is nevertheless a need for a new intervertebral device that includes self-contained anchoring members that deploy in response to rotational, pulling, or pushing driving forces.

SUMMARY OF THE INVENTION

Embodiments of the present invention are stand-alone interbody devices, which may be designed in the general style of an anterior lumbar interbody fusion (ALIF) device, a transforaminal lumbar interbody fusion (TLIF) device, a posterior lumbar interbody fusion (PLIF) device, or a far anterior lateral interbody fusion (FALIF) device. In addition, the size and/or shape of the basic embodiments disclosed herein may be adapted by the skilled artisan for use in various levels of the spine, namely the cervical spine, the thoracic spine, and the lumbar spine. Thus, while various embodiments herein may be described by way of example with respect to the lumbar spine, such disclosures apply with equal weight to the other levels of the spine.

The device includes a body made from any variety of structural biomaterial including, but not limited to, any of a number of biocompatible implantable polymers, including PEKK, PEKEK, polyetheretherketone (PEEK) being preferred, Titanium, ceramic, etc. The external body surface may have a variety of surface textures, surface coatings, and surface geometries, including serrated superior and/or inferior surfaces to provide initial resistance against migration. Additionally, there may be at least one opening extending from the superior surface to the inferior surface for the purpose of containing a family of graft materials, such as autograft, bone morphogenetic protein (BMP), bone marrow aspirate/concentrate, etc.

The body contains at least one anchor therein, which may be deployed from the body of the device via a drive mechanism through an associated aperture. The at least one anchor penetrates the vertebral bone adjacent to the device to secure the device in place.

In accordance with one or more embodiments, a prosthesis includes: a body including a first major surface for engaging an endplate of a first vertebral bone of a spine, a second major surface for engaging an endplate of an adjacent, second vertebral bone of the spine; at least one aperture extending from within the body and opening at the first major surface; at least one anchoring element disposed within the aperture and including a shaft having proximal and distal ends; and a drive mechanism engaging the proximal end of the at least one anchoring element and operating to push the at least one anchoring element out through the at least one aperture and into the first vertebral bone, without rotating the at least one anchoring element about an axis defined the length of the anchoring element itself, i.e., the major axis of the anchoring element.

One of the benefits of the embodiments of the invention is the ease with which the devices may be used. There are fewer steps as compared with conventional devices because at least one (and preferably all) of the anchors can be deployed from the body of the device using the same tool from inserting the device into the intervertebral space. Furthermore, because the anchors are self-contained, there is no difficult trajectory needed to place and tighten screws as with previous devices.

Other aspects, features, advantages, etc. will become apparent to one skilled in the art when the description of the preferred embodiments of the invention herein is taken in conjunction with the accompanying drawings.

BRIEF DESCRIPTION OF THE DRAWINGS

For the purposes of illustrating the various aspects of the invention, there are shown in the drawings forms that are presently preferred, it being understood, however, that the invention is not limited to the precise arrangements and instrumentalities shown.

DETAILS OF THE EMBODIMENTS OF THE INVENTION

Figure 1A:
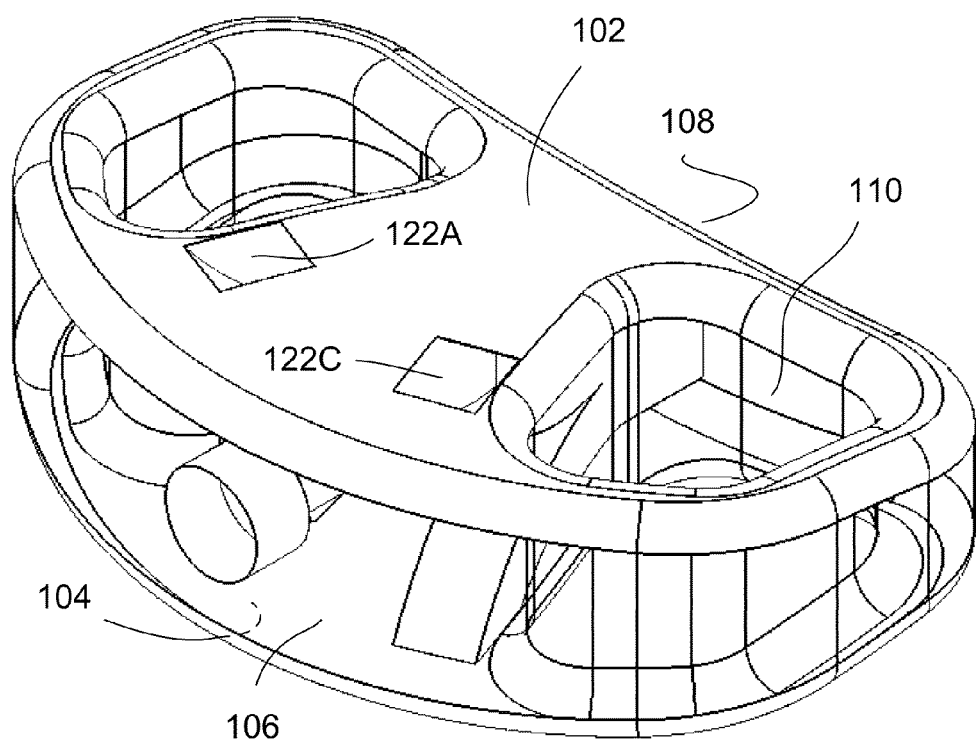
FIG. 1A is a perspective view of an intervertebral prosthetic device in accordance with one or more embodiments of the present invention.
Figure 1B:
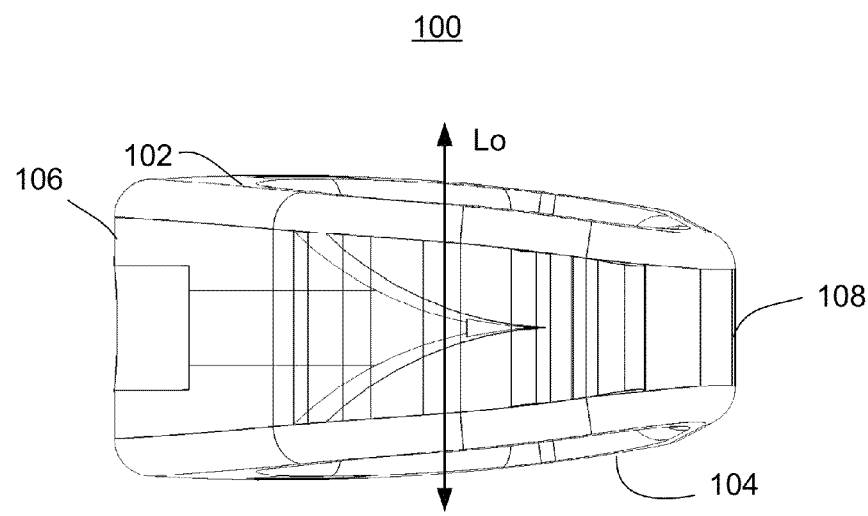
FIG. 1B is a side (lateral) view of the intervertebral device of FIG. 1A.
Figure 1C:
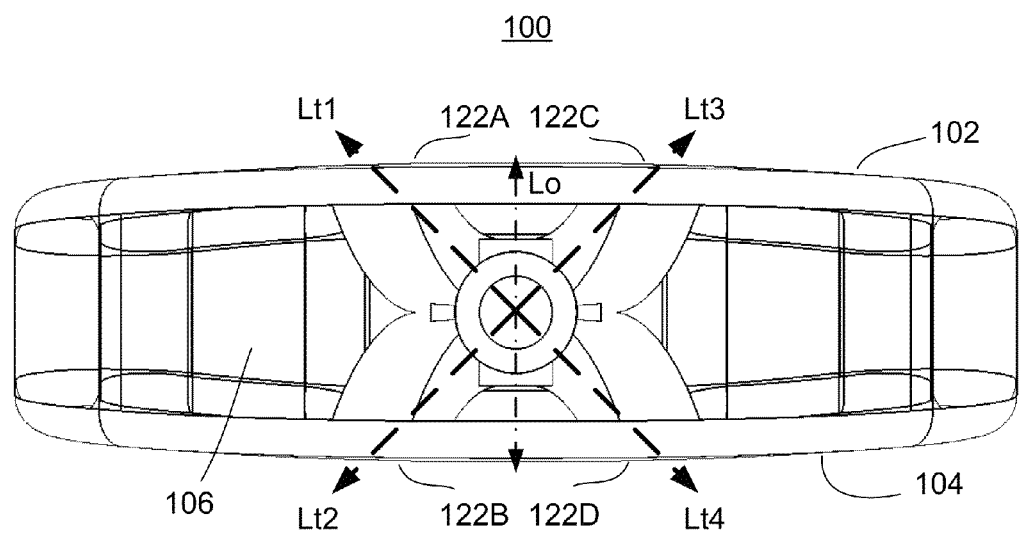
FIG. 1C is an anterior elevational view of the intervertebral device of FIG. 1A.

Reference is now made to FIGS. 1A, 1B, and 1C, which illustrate an intervertebral prosthetic device 100 in accordance with one or more embodiments of the present invention. FIG. 1A illustrates a perspective view of the intervertebral device 100. FIG. 1B is a lateral (side) view with the left of the drawing being in the front (anterior) direction and the right of the drawing being in the rear (posterior) direction. FIG. 1C is an anterior elevational view of the intervertebral device 100.

The body of the device may be made from any biocompatible material, such as any of a number of biocompatible implantable polymers, including PEKK, PEKEK, polyetheretherketone (PEEK) being preferred, titanium, ceramic, etc.

Figure 2:
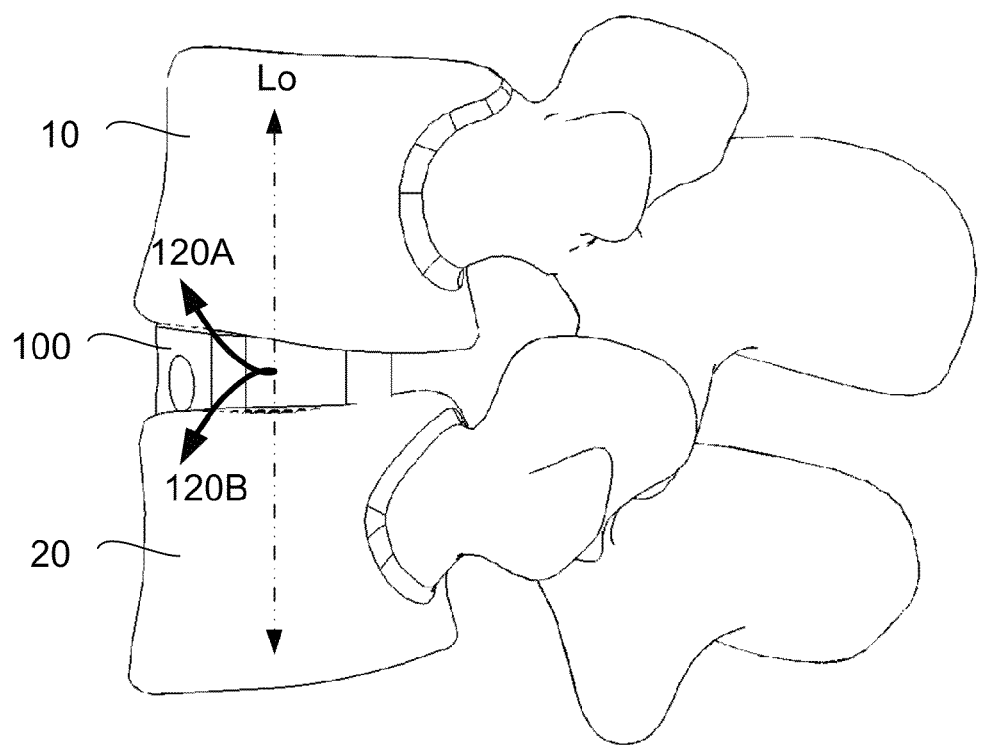
FIG. 2 is an illustration of the intervertebral device of FIG. 1 in use.

With further reference to FIG. 2, which shows the device 100 in use, the device 100 generally includes a body (or housing) that is sized and shaped to fit in the intervertebral space between adjacent vertebral bones 10, 20 of the human spine. It is understood that the size and shape of the device 100 may be adapted to fit in an intervertebral space at any level of the spine, such as the cervical spine, thoracic spine, or lumbar spine. The intervertebral device 100 as illustrated in this example is designed to be a stand-alone device (e.g., requiring no separate anchoring devices), which is inserted into the intervertebral space from an anterior direction. This embodiment is in the general form of an ALIF device, although as will be appreciated from the description herein, the device may be adapted to operate as a TLIF device, far anterior lateral interbody device, PLIF device, used in any level of the spine. In these latter cases, the device may be introduced into the intervertebral space from a direction other than anterior.

The body includes first and second spaced apart major surfaces 102, 104 and at least one sidewall 106, 108 extending therebetween. In the embodiment of an ALIF, the sidewalls 106, 108 may be directed in the anterior and posterior direction, respectively. Given the general geometry of the body of the device 100, the sidewalls may also include sidewalls, or portions, directed generally in the lateral (medial) directions. The first major surface 102 operates to engage an endplate of the first vertebral bone 10 of the spine, and the second major surface 104 operates to engage an endplate of the adjacent, second vertebral bone 20 of the spine. As best seen in FIGS. 1B and 2, the first and second major surfaces 102, 104 define a longitudinal axis Lo extending substantially normal to said surfaces and either coaxial with, or generally parallel to, the longitudinal direction of the spine. With reference to FIGS. 1B and 1C, it is understood that the longitudinal axis Lo is not precisely normal to the first and second major surfaces 102, 104 as there is a slight narrowing height (taper) to the body from the sidewall 106 to the sidewall 108. This taper is designed to accommodate the natural anatomic relationships between the adjacent vertebral bones 10, 20, thereby maintaining the normal lordodic curvature of the spine.

The surgery involved with implanting the device 100 involves removal of the disc material from the intervertebral space, release of the contracted soft tissues around the disc space, and some degree of distraction or pulling apart of the adjacent vertebrae 10, 20 in an attempt to mechanically restore disc space height, realign the anatomical axis of the spine, and indirectly decompress the nerve roots exiting the spine posteriorly at the particular level. After the surgeon removes the disc material, a clean aperture (space) is achieved in which to place the device 100. The surgeon may use a tool to simultaneously grasp the body of the device 100, place it at the mouth of the intervertebral space, and apply force so that the device 100 achieves its final placement.

In order to facilitate desirable mechanical interface between the endplates of the respective vertebral bones 10, 20 and the device 100, one or both of the first and second major surfaces 102, 104 of the body include a bone engagement feature, such as at least one of serrations, protrusions, valleys, spikes, knurling, keels, etc. (not shown). Additionally or alternatively, the intervertebral prosthesis 100 may include one or more apertures 110 extending between and through at least one of the first and second major surfaces 102, 104 of the body that operate to permit dense osseous growth between the body of the prosthesis 100 and the one or more vertebral bones 10, 20.

As illustrated in FIG. 2, once the surgeon has manipulated the device 100 into its proper orientation within the intervertebral space, one or more anchoring elements 120A, 120B are deployed from within the body and engage one or more of the vertebral bones 10, 20. Notably, and as will be discussed in more detail below, the one or more anchoring elements 120A, 120B are pushed out of the body and into the first vertebral bone, without rotating any of the anchoring elements about a major axis thereof, defined by the length of the anchoring element itself. For example, the deployment of the one or more anchoring elements 120A, 120B is not accomplished by threading the anchoring element into the vertebral bones 10, 20. As will also be described in more detail herein, the anchoring elements 120A, 120B deploy from the body into the vertebral bones 10, 20 in directions transverse to the longitudinal axis Lo of the body and the spine.

Figure 3A:
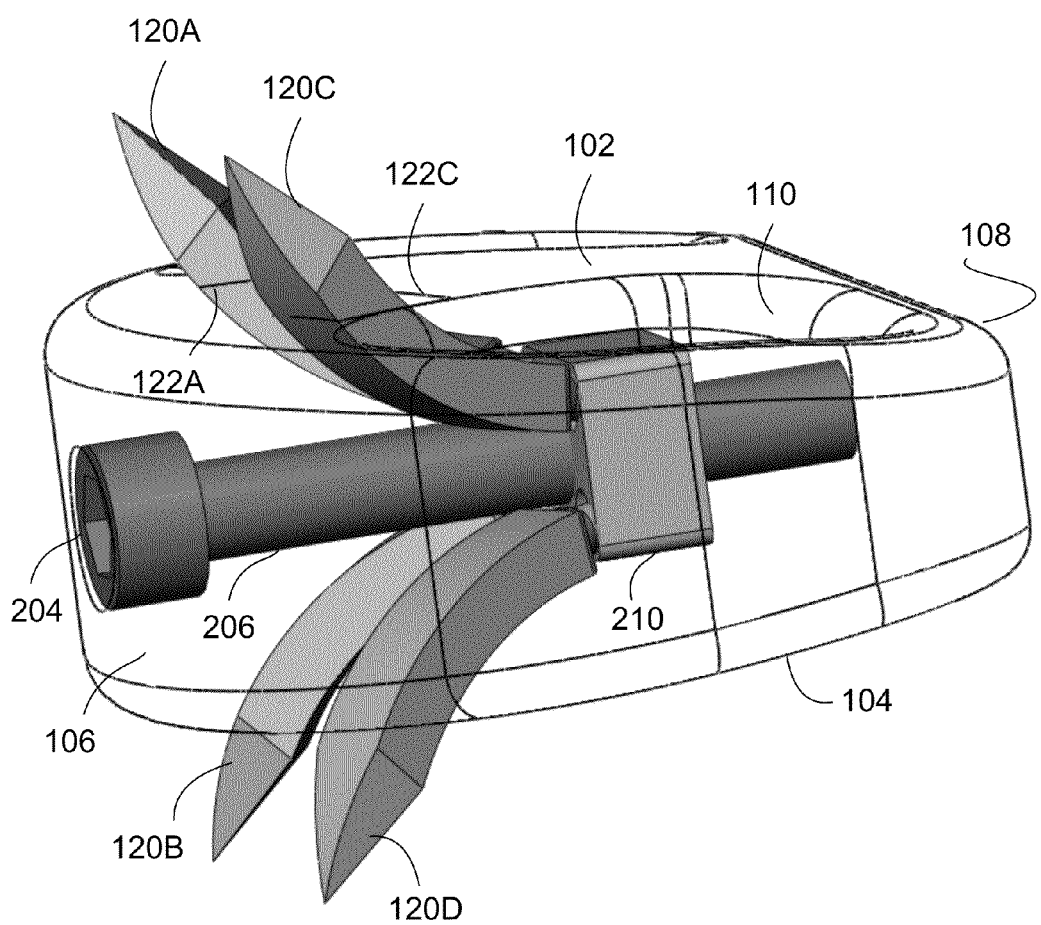
FIG. 3A is a partial see-through lateral-perspective view of the intervertebral prosthetic device of FIG. 1A showing an example of the inner construction of the device.

Reference is now made to FIGS. 1A, 1B, 1C, and 3A, where FIG. 3A is a partial see-through lateral-perspective view of the intervertebral prosthetic device of FIG. 1A showing an example of the inner construction of the device. The body of the device includes at least a first aperture 122A extending from within the body, transversely with respect to the longitudinal axis Lo, and opening at the first major surface 102. Preferably, there is a plurality of apertures, with four such apertures 122A, 122B, 122C, 122D being preferred.

A first anchoring element 120A is disposed within the first aperture 122A in a manner in which deployment of the anchoring element 120A results in a trajectory out of the body and into the given vertebral bone in a direction transverse to the longitudinal axis Lo of the body and the spine. Preferably, there is a respective anchoring element 120A, 120B, 120C, 120D disposed within each of the apertures 122A, 122B, 122C, 122D in a manner in which deployment of each anchoring element 120 results in a respective trajectory out of the body transverse to the longitudinal axis Lo of the body and the spine.

Preferably, each anchoring element 120A, 120B, 120C, 120D is in the form of a shaft having a proximal end and a distal end 124A. Each anchoring element 120 may also include a sharp point at the distal end 124A to facilitate penetration into the vertebral body in response to a pushing force at the proximal end.

Although shown in FIG. 3A with a square cross-section, each anchoring element 120 may have any suitable shape, such as one of: (i) smooth, concentric ringed partially or fully, ribbed, barbed, of multi-lateral cross-section, of quadrilateral cross-section, of trilateral cross-section, of curvilinear cross-section, and of circular cross-section. The associated apertures 122 may be characterized by smooth walls that permit the anchoring elements 120 to slide and translate therethrough during deployment. Although the cross-section of the apertures 122 may be of any suitable shape that permits such sliding, a complementary shape to the cross-section of the anchoring elements 120 is desirable. The concentric ring shaped is the preferred embodiment due to its substantial holding power and back out strength.

Notably, the shaft of each anchoring element 120 is arced along its length. The arc better facilitates translation and penetration of the anchoring element 120 into the vertebral bone during deployment. Depending on the exigencies of the application, some or all of the anchoring elements 120 may have arced or straight shafts. When arced, it is preferred that the radius of curvature is between 3 mm to about 30 mm, with about 10-15 mm being preferred, and about 12 mm being most preferred for use in the lumbar spine. The measurement of the radius of curvature is from a fulcrum to a farthest (outside) edge of the anchor 120.

As noted above, one or more of the apertures 122A, 122B, 122C, 122D extend within the body transversely with respect to the longitudinal axis Lo, and each opens at one or the other of the first and second major surfaces 102, 104. In this sense the apertures may be considered as channels extending through the body in order to guide the anchors 120 to their destination and to ensure a proper deployment direction for each anchor 120. When a given anchor 120 is straight, then the associated aperture/channel 122 is also preferably straight. When a given anchor 120 is arced, then the associated aperture/channel 122 is also preferably arced. When arced, the radius of curvature of the aperture/channel 122 may be any suitable magnitude that permits the sliding and guiding function; however, a complementary radius of curvature (which need not be exactly the same) as compared to the radius of curvature of the associated anchoring element 120 is desirable.

Figure 3B:
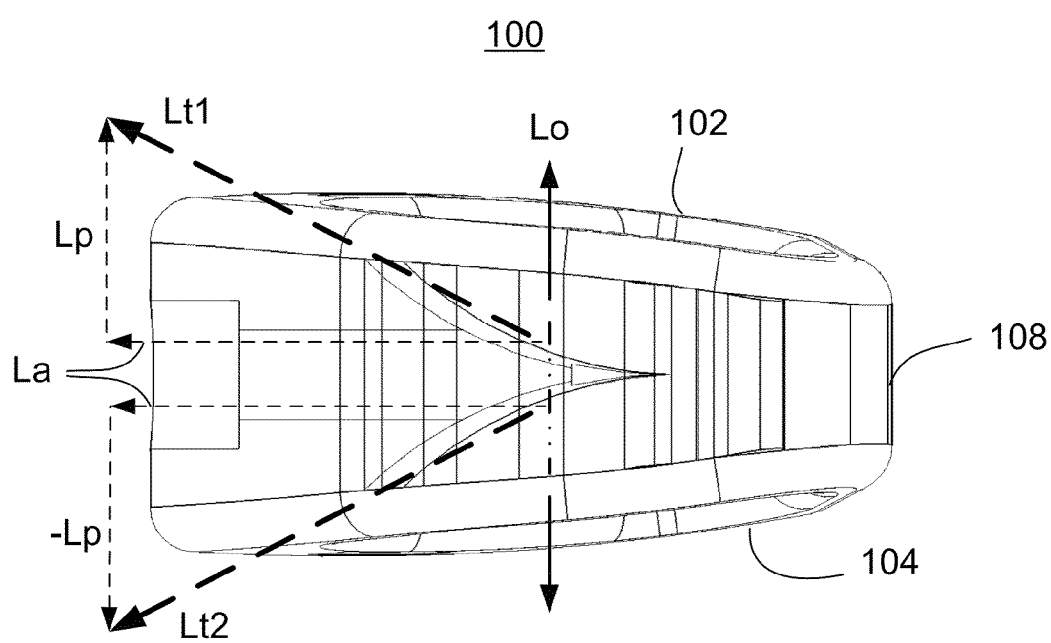
FIG. 3B is a lateral elevational view of the intervertebral prosthetic device of FIG. 3A showing a schematic view of deployed anchors and directions of deployment.

With reference to FIG. 3B, the respective trajectories Lt of the anchoring elements 120 is of importance to achieving desirable fixation of the device 100 within the intervertebral space and avoidance of later migration during use. In this regard, the size, shape, and orientation of the first aperture 122A, and thus the direction of deployment Lt1 of the first anchoring element 120A therefrom, is transverse to the longitudinal axis Lo of the body. In general, when an anchoring element 120$i$ is straight, then the direction of deployment may be considered to be along the straight longitudinal axis of the anchor shaft. When the anchoring element 120$i$ is arced, then there are some options for defining the direction of deployment.

First, even though the anchoring element 120$i$ is arced and may deploy through an arc, for purposes of simplicity, the deployment direction Lt1 is nevertheless defined in terms of straight component vectors in a 2D or 3D coordinate system. Second, the direction of deployment Lt1 is defined as a straight composite vector of the component vectors in association with the corresponding arced anchoring element 120$i$. One option for defining such association is to assume that the straight composite vector starts at one point along the arced anchoring element 120$i$ and passes through at least one other point along the anchoring element 120$i$. For example, the composite vector may start at the proximal end of the anchoring element 120$i$ and passes through another point, such as the tip of the anchoring element 120$i$. Alternatively, the composite vector may start somewhere intermediate along the anchoring element 120$i$ and pass through the tip of the anchoring element 120$i$. Another example is to use two points, neither of which are at the proximal or distal extremes of the anchoring element 120$i$. In a further alternative, the defined association may not assume that the straight composite vector passes through more than one point along the anchoring element 120$i$, but rather is tangential to a single point along the arced anchoring element 120$i$.

For purposes of the example illustrated, it is assumed that the straight composite vector representing the first direction of deployment Lt1 starts at or near the proximal end of the first anchoring element 120A and passes through an intermediate point. The first deployment direction Lt1 includes a first substantial directional component La in an anterior direction of the body (toward the sidewall 106). The deployment direction Lt1 also includes a second substantial directional component Lp parallel to the longitudinal axis Lo of the spine. These components of trajectory, Lt=La+Lp, in the anterior and longitudinal directions characterize a significant difference with certain prior art techniques, where the deployment is fully in the longitudinal direction of the spine. In a further difference with certain prior art techniques, the anchoring element(s) 120 is/are pushed out of the body and into the vertebral bone, without rotating the anchoring element(s) 120 about an axis thereof. For example, the deployment of the anchoring element(s) 120 is not accomplished by threading the anchoring element(s) 120 into the vertebral bones 10, 20. Further, the deployment of the anchoring element(s) 120 is not accomplished by mere rotation thereof about a hinged end. Indeed, as will be discussed further later herein, the ends of the anchoring element(s) 120 that remain within the intervertebral prosthesis 100 during deployment, actually move translationally during deployment.

The size, shape, and orientation of the second aperture 122B, and thus the direction Lt2 of deployment of the second anchoring element 120B therefrom, is also transverse to the longitudinal axis Lo of the body. More particularly, the deployment direction Lt2 includes a first substantial directional component La in an anterior direction and second substantial directional component −Lp parallel to the longitudinal axis Lo of the body and opposite to the second substantial directional component Lp of the deployment direction Lt1 of the first anchoring element 120A.

Although not shown in detail in FIG. 3B, similar characteristics and comparisons may be made to the deployments directions Lt3 and Lt4 of the third and fourth anchoring elements 120C, 120D.

Figure 3C:
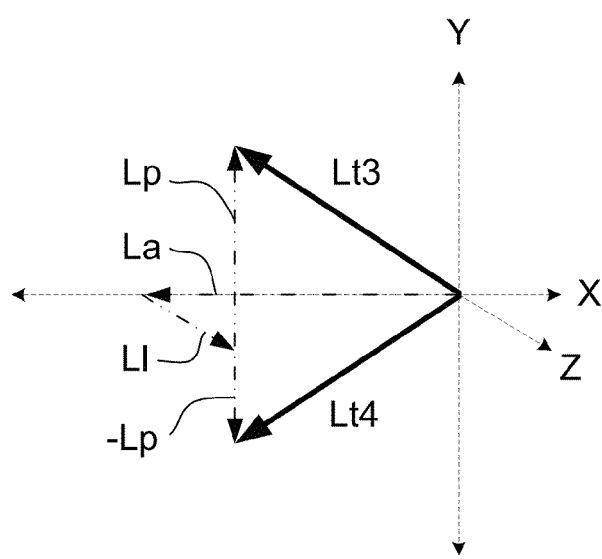
FIG. 3C is a schematic, 3-D orthogonal coordinate view of directional components of the anchoring elements of the intervertebral prosthetic device of FIG. 3A.

Reference is now made to FIG. 3C, which is a schematic 3-D view of directional components of deployments directions Lt3, Lt4 of the third and fourth anchoring elements 120C, 120D of the intervertebral prosthetic device of FIG. 3A. The third deployment direction Lt3 of the third anchoring element 120C includes: (i) a first substantial directional component in one of an anterior and posterior direction of the body (in this example La); (ii) a second substantial directional component Lp parallel to the longitudinal axis Lo of the body; and (iii) a third substantial directional component Ll in a lateral direction with respect to the anterior-posterior direction of the body.

Similarly, the fourth deployment direction Lt4 of the fourth anchoring element 120D includes: (i) a first substantial directional component in one of an anterior and posterior direction of the body (again La in this example); (ii) a second substantial directional component Lp parallel to the longitudinal axis of the body (but opposite of the Lp of the third deployment direction Lt3); and (iii) a third substantial directional component Ll in a lateral direction with respect to the anterior-posterior direction of the body (which is parallel with the third substantial directional component Ll of the third deployment direction Lt3).

With reference to FIGS. 1C, 3A and 3B, in one or more embodiments the deployment directions Lt1 and Lt2 may also include lateral components Ll. Notably, the lateral component Ll (which has been referred to as the third substantial directional component in the examples above) of each of the deployment directions Lt1 and Lt2 are in the same direction, but are opposite to the lateral components Ll of the deployment directions Lt3 and Lt4. More generally, at least two of the first, second, and third substantial directional components of either of the third or fourth deployment directions Lt3, Lt4 will be substantially opposite to the respective first, second, and third substantial directional components of at least one of the first and second deployment directions Lt1, Lt2 and vise verse.

With reference to FIGS. 1C and 3A, it is noted that the above-described relationships of the vector components of the respective deployment directions Lt1, Lt2, Lt3, Lt4 reveal an interesting characteristic of the collection of deployments. In particular, in some embodiments, the collection of deployments is characterized by: (i) a point of origin where all of the actual paths of the deployment (whether arced or straight) intersect, and (ii) an expansion radially away from the point of origin. The characteristics of the radial expansion include that the respective paths do not all lay in the same plane.

Generally, the first and second anchoring elements 120A, 120B deploy divergently to one another at an arced angle of greater than about 40°. Similarly, the third and fourth anchoring elements 120C, 120D also deploy divergently to one another at an arced angle of greater than about 40°.

The anchoring characteristics of the device 100 within the intervertebral space may be adjusted by adding or removing any number of individual anchoring elements 120. Indeed as discussed above, as the size and/or shape of the basic device 100 may be adapted for use in the cervical spine, the thoracic spine, and/or the lumbar spine, so too may the number of individual anchoring elements 120 be adjusted. For example, a lesser number of anchoring elements 120 might be desirable in the cervical spine than in the thoracic spine and/or the lumbar spine. In addition, the particular deployment directions of the individual anchoring elements 120 may be adjusted in order to best suit the particular physical bone geometries found in the various levels of the spine.

In one or more embodiments, such as the device 100 of FIGS. 1A-3B, a first pair of anchoring elements 120A, 120B may be disposed at one lateral side of the body, and a second pair of anchoring elements 120C, 120D (of similar construction) may be disposed at another opposite lateral side of the body. In this embodiment, each of the anchoring elements 120 exhibits a deployment trajectory having a substantial component in the anterior direction La (opposite to the posterior direction).

The above examples disclose a device in which the third lateral component Ll of the directional components of Lt1, Lt2, Lt3, Lt4 are all directed outwardly. It is noted, however, that one or all of the lateral components Ll may be directed medially by suitable redirection of the associated aperture.

Figure 4:
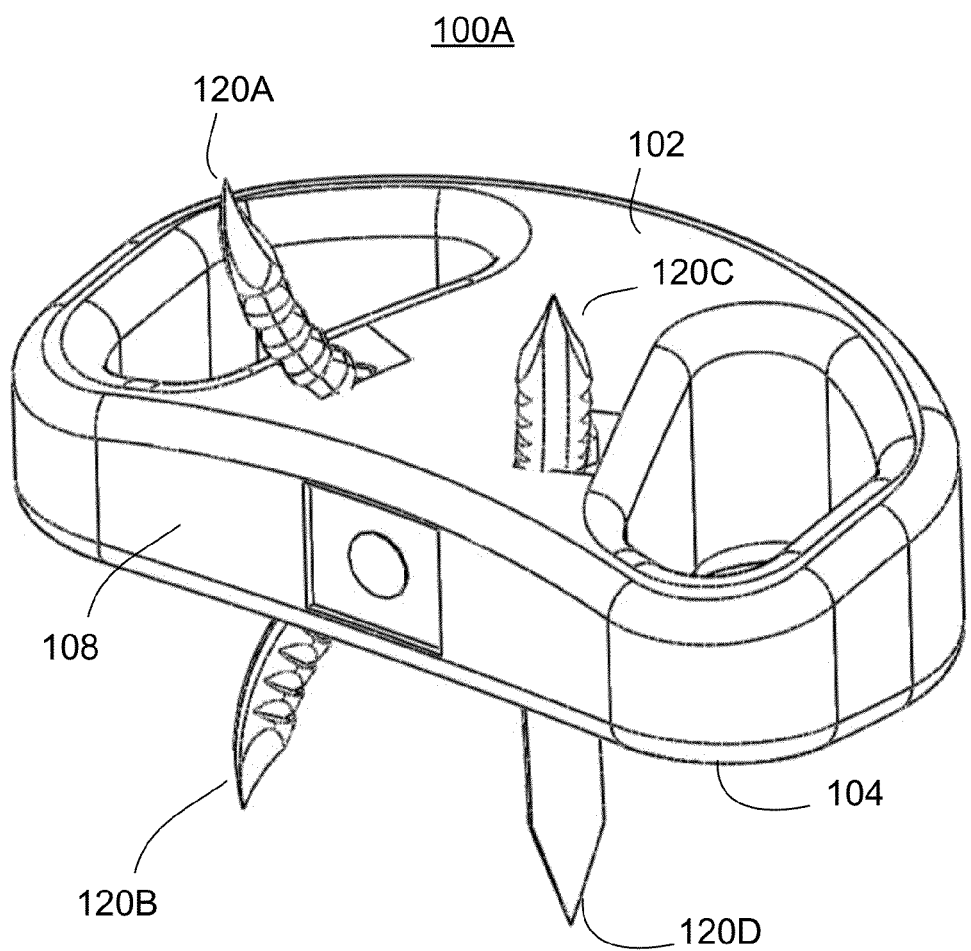
FIG. 4 is a posterior-perspective view of an intervertebral prosthetic device with alternative deployment directions and with anchoring elements deployed.

Reference is now made to FIG. 4, which is a posterior-perspective view of an intervertebral prosthetic device 100A with alternative deployment characteristics as compared with the intervertebral prosthetic device 100. In this view of the intervertebral prosthetic device 100A, the anchoring elements are in a deployed state. The anchoring characteristics of the device 100A include first and second pairs of anchoring elements 120A, 120B and 120C, 120D disposed at opposite lateral sides of the body. In a notable difference with the device 100, each of the anchoring elements 120 of the intervertebral prosthetic device 100A exhibits a deployment trajectory having a substantial component in the posterior direction (i.e., in the −La direction). This is essentially opposite to the deployment of the anchoring elements 120 in the device 100.

Figure 5A:
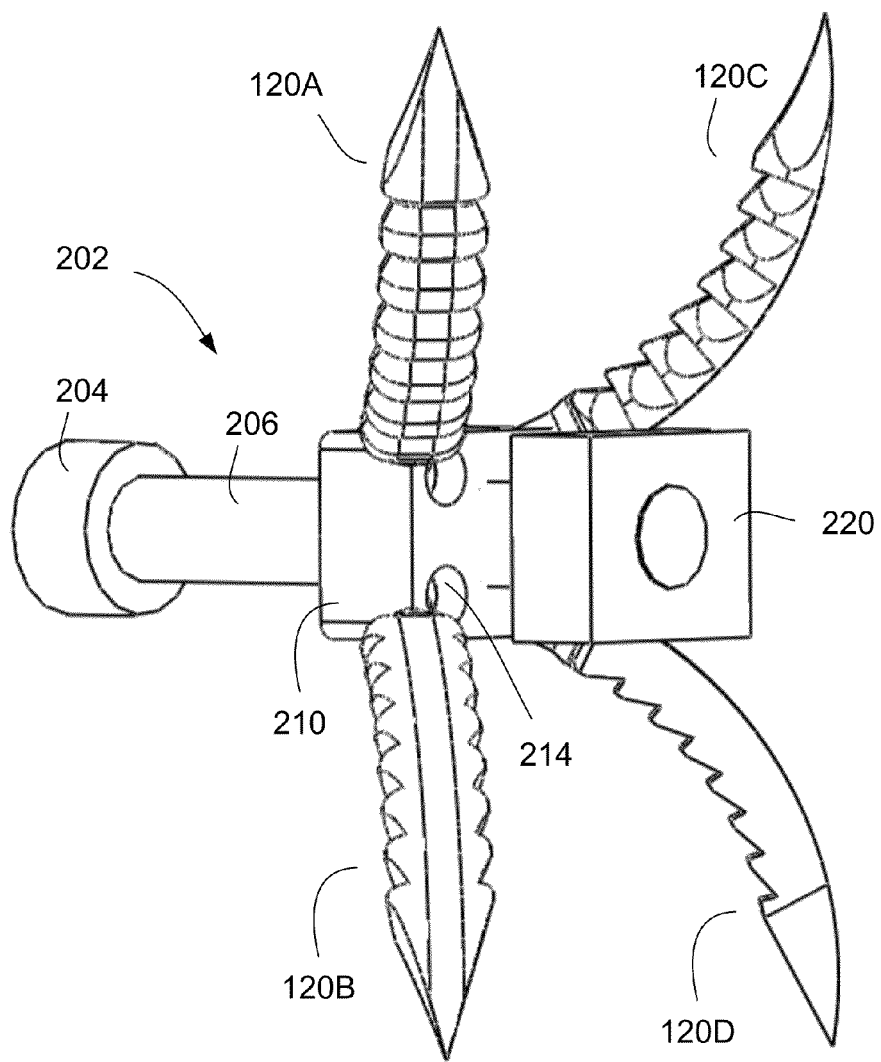
FIG. 5A is a perspective view of certain of drive mechanism components in cooperation with anchoring elements shown outside the body of the intervertebral prosthetic device.
Figure 5B:
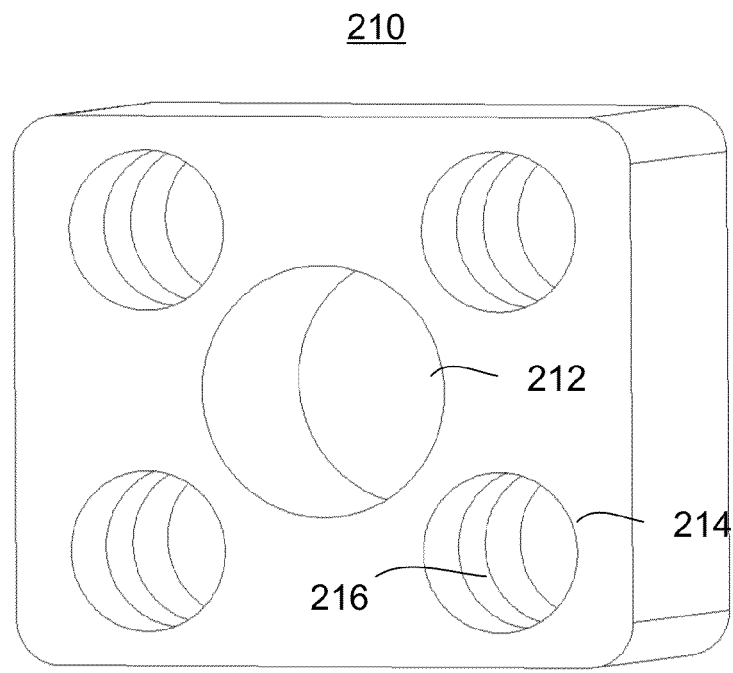
FIG. 5B is a perspective view of a translator element of the drive mechanism of FIG. 5A.
Figure 5C:
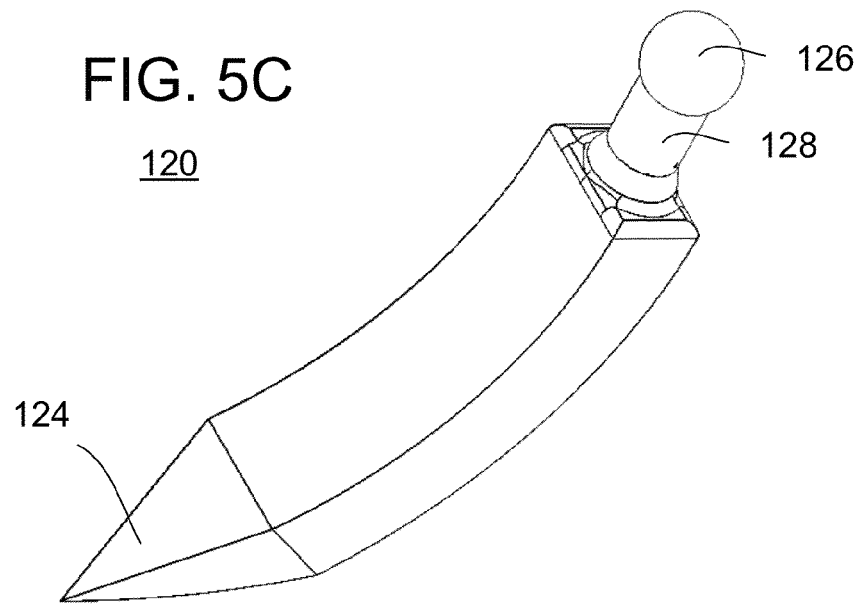
FIG. 5C is a perspective view of an anchoring element shown without engagement to the drive mechanism of FIG. 5A.

Reference is now made to FIGS. 5A, 5B, and 5C, which illustrate additional details of the intervertebral prosthetic device 100 (or 100A). FIG. 5A is a perspective view of the main components of a drive mechanism 200, shown in cooperation with four anchoring elements 120. The perspective view shown in FIG. 5A is from an opposite lateral point of view with comparison to the visible components of the drive mechanism 200 shown in FIG. 3A.

At the core, the drive mechanism 200 engages the proximal end of one or more (preferably all) of the anchoring elements 120 and operates to push the anchoring elements 120 out through the respective apertures 122 and into the vertebral bones. This is accomplished without rotating any of the anchoring elements 120 along a longitudinal axis thereof. Notably, when a plurality of anchoring elements 120 are employed, the drive mechanism 200 preferably deploys all of the anchoring elements 120 simultaneously, at the same rate and via substantially the same translational force.

The drive mechanism 200 includes a drive shaft 202 having a head 204 at a proximal end and a threaded shaft 206 extending therefrom. The longitudinal extension of the drive shaft 202 defines a longitudinal axis thereof. The drive mechanism 200 also includes a translator element 210, which engages each of the proximal ends of the one or more anchoring elements 120. As best seen in FIG. 5B, the translator element 210 includes a threaded bore 212 that is in threaded engagement with the threaded shaft 206 of the drive shaft 202. The translator element 210 also includes at least one, and preferably an equal number of coupling elements 214 as there are anchoring elements 120. Each coupling element 214 is in engagement with, captivates, but permits articulation of the proximal end of a respective one of the anchoring elements 120. With reference to FIGS. 5B and 5C, each of the coupling elements 214 includes a socket 216 and the proximal end of each anchoring element 120 includes a ball 126. The ball 126 may be offset from the terminus of the anchoring element 120 by way of a relatively short shaft 128. The ball 126 is captive within the socket 216 such that the translator 210 is in engagement with, and permits articulation of, the proximal end of the anchoring element 120 during movement along the longitudinal axis of the drive shaft 202. It is noted that such articulation may include any number of degrees of movement; however, in accordance with at least one embodiment, the articulation permits movement of the proximal end (and the distal end for that matter) of the anchoring element 120 in more than one (and preferably many) axes of rotation as one would expect from a ball-and socket arrangement as compared with a hinge arrangement (which permits movement about a single axis of rotation).

The drive shaft 202 is oriented in an anterior-to-posterior direction within the body of the device 100 (or 100A), with at least the head 204 thereof accessible external to the body such that a rotational force may be applied to the head 204 by an operator of the device. In the embodiment of FIG. 3A, the drive shaft 202 is oriented in an anterior-to-posterior direction within the body of the device 100 such that the head 204 is accessible at the anterior side of the device 100. In the embodiment of FIG. 4, the drive shaft 202 is oriented in an anterior-to-posterior direction within the body of the device 100A such that the head 204 is also accessible at the anterior side of the device 100. The major difference then in the orientation of the driving mechanism 200 within the respective devices 100 and 100A is that the anchoring elements 120 of the former engage and extend away from one side of the translator element 210 within the body, while those of the latter engage and extend away from an opposite side of the translator element 210 within the body.

Irrespective of which device orientation is employed, the drive shaft 202 is fixed in the direction of the longitudinal axis thereof, but rotatable, within the body in response to a rotational force applied to the head 204. In order to stabilize the orientation of the drive shaft 202 within the body, a bearing 220 may be employed at a distal end of the shaft 206, opposite to the head 204. The rotation of the drive shaft 202 cause a corresponding rotation of the threaded shaft 206 within the threaded bore 212 of the translator device 210. Such rotation causes the translator device 210 to move translationally along the longitudinal axis of the drive shaft 202 and push the anchoring element(s) 120 out through the respective aperture(s) 122 and into the vertebral bone. The cooperation between the drive shaft 202 and the translator element 210 produces a tremendous amount of translational (pushing) force, which is sufficient to drive the anchoring element(s) 120 out through the respective aperture(s) 122 and into the vertebral bone without requiring threading (rotation) of the anchoring elements 120 into the bone. Notably, the translator device 210 causes the proximal ends of the anchoring element(s) 120 to move translationally parallel to the longitudinal axis of the drive shaft 202. In this sense, deployment is not accomplished by mere rotation of the anchoring element(s) 120 about stationary proximal ends thereof, but rather through pushing, translational movement of the proximal ends of the anchoring element(s) 120.

Figure 6:
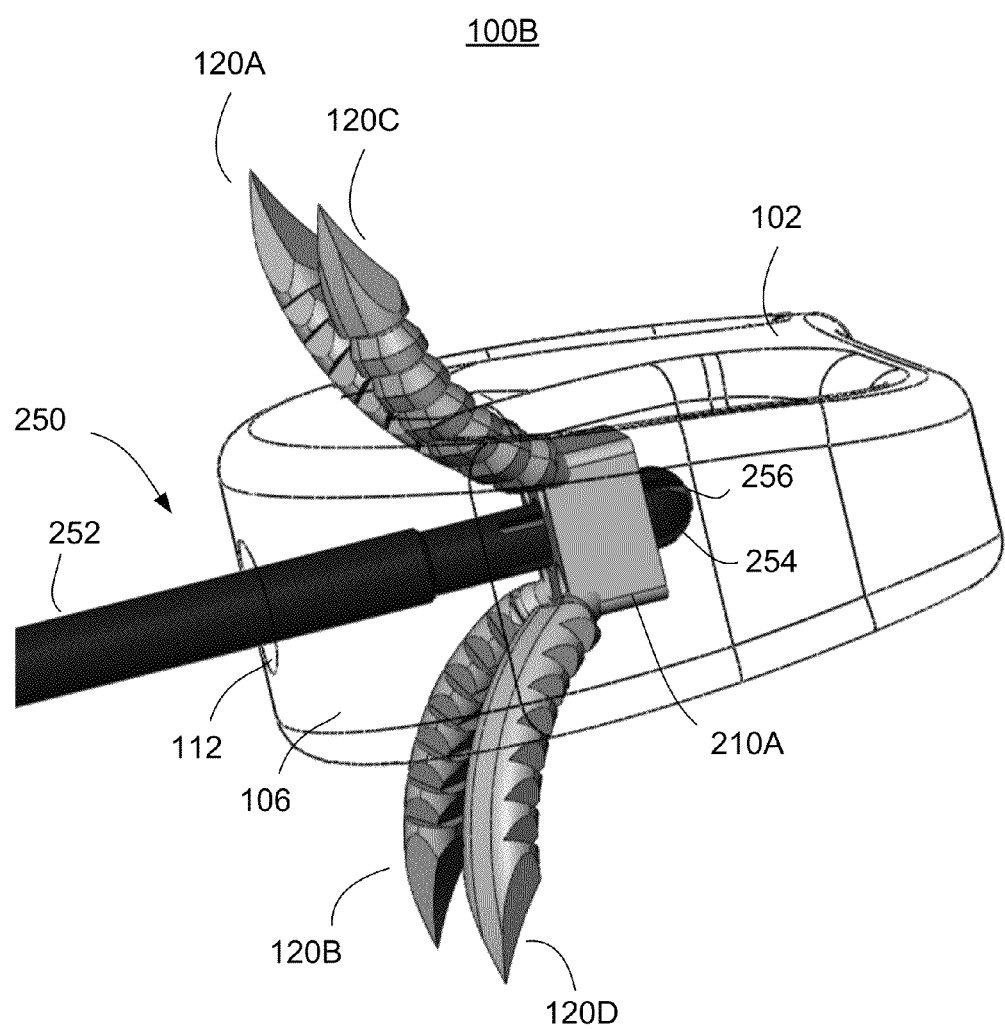
FIG. 6, illustrates an alternative drive mechanism to deploy the anchoring elements from the device.

Reference is now made to FIG. 6, which illustrates an alternative device 100B having a different drive mechanism to push, pull, or twist the anchoring elements 120 through the respective apertures 122. In this embodiment, the drive mechanism includes some components disposed within the body of the device 100B and one or more external elements. In particular, the device 100B includes a translator element 210A, which engages each of the proximal ends of the one or more anchoring elements 120. The translator element 210A may substantially similar to the translator element 210 discussed above, and includes a bore therethrough which may be non-threaded. The drive mechanism, however, does not include the drive shaft 202. Instead, an external shaft element 250 is employed to enter an aperture 112 of the body and engage the bore of the translator element 210A.

In particular, the shaft element 250 includes an extension (or rod) 252 that is manipulated by an operator and a distal end 254, which includes an engagement feature. The engagement feature exhibits a releasable connection to the translator element 210A (such as to the bore) and permits the operator to push, pull, or twist the anchoring elements 120 through the respective apertures 122. In the illustrated embodiment, the shaft 252 is hollow along its length and includes a fluted distal end 254 (which may include an optional tapered undercut). The flutes permit the distal end 254 to flex and press into and through the bore of the translator element 210A. Once the distal end 254 is in place, a rod 256 is inserted into the proximal end of the shaft 252 (not shown) and is slid all the way to the distal end 254, proximate to the flutes. The presence of the rod 256 prevents re-flexing of the flutes and prevents the tapered undercut from pulling back through the bore of the translator element 210A. At this point, the operator may push, pull and/or twist the translator element 210A to achieve desirable movement of the anchoring elements 120.

In the example in which the device 100B shown in FIG. 6 is an ALIF, the translator element 210A is movable such that movement thereof along a longitudinal axis in an anterior-posterior direction, pushes or pulls the at least one anchoring element out through the at least one aperture and into the first vertebral bone, without rotating the at least one anchoring element about a major axis thereof. In an alternative example in which the device may be adapted for far anterior lateral insertion, the translator element 210A is movable such that movement thereof along a longitudinal axis in first and second opposing lateral directions, pushes or pulls the at least one anchoring element out through the at least one aperture and into the first vertebral bone, without rotating the at least one anchoring element about a major axis thereof.

When the operator has completed the deployment of the anchoring elements 120, he/she may withdraw the rod 256 at least as far as needed to permit the flexing of the flutes, and then withdraw the distal end 254 of the shaft element 250 from the bore of the translator element 210A. Those skilled in the art will appreciate that there are many other ways to achieve the releasable connection between the shaft element 250 and the translator element 210A. For example, the bore of the translator 210A may be threaded and the distal end 254 of the shaft element 250 may be threaded to achieve the desirable connectivity.

Figure 7:
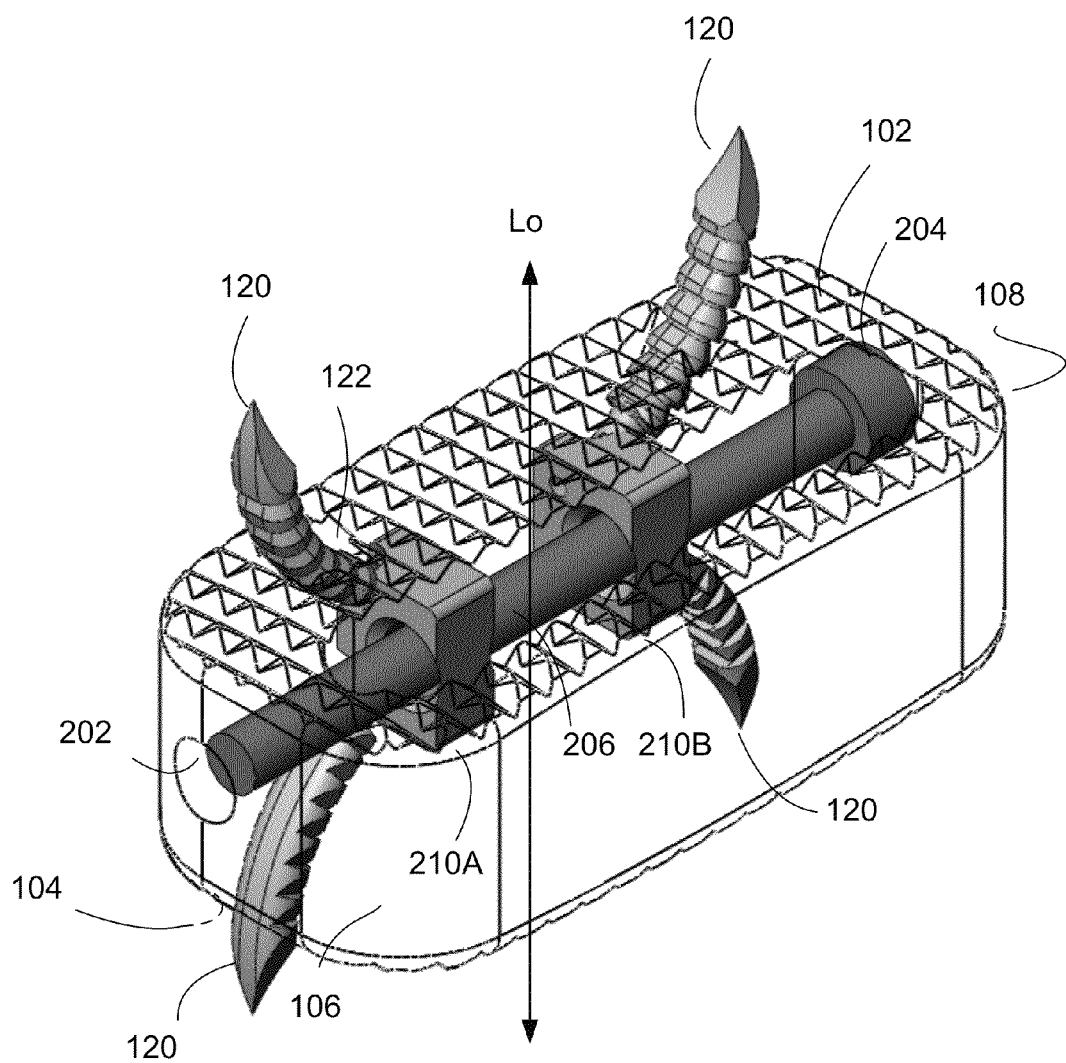
FIG. 7 is a perspective view of an intervertebral prosthetic device with alternative characteristics (with anchoring elements deployed).

Reference is now made to FIG. 7, which illustrates an alternative device 100C having an alternative drive mechanism to push the anchoring elements 120 through the respective apertures 122. By way of example, the embodiment of FIG. 7 may be particularly suited for far anterior lateral interbody fusion, owing to the more rectangular shape as compared with the other devices 100, 100A, 100B. Thus, with reference to FIG. 2, the device 100C may be implanted from a first lateral direction, or a second opposing lateral direction (into or out of the page).

In this embodiment, the drive mechanism includes substantially the same components disposed within the body of the devices 100, 100A, or 100B (see, also FIG. 5A) with some modification. In particular, the device 100C includes at least two translator elements 210A, 201B, each having the aforementioned threaded bore 212 for threaded engagement with the threaded shaft 206 of the drive shaft 202. Each of the translator elements 210A, 201B is coupled to a respective at least one anchoring element 120 (for a total of four anchoring elements by way of example). The threaded shaft 206 includes first and second portions, the first portion being threaded in a first direction, and the second portion being threaded in a second direction, opposite to the first direction. The first translator element 210A is in threaded engagement with the first portion of the threaded shaft 206, while second translator element 210B is in threaded engagement with the second portion of the threaded shaft 206.

Deployment of the respective sets of at least one anchoring element 120 is accomplished in a manner similar to one or more of the approaches discussed above. For example, the rotational force applied to the shaft 202 causes the respective first and second threaded portions of the threaded shaft 206 to rotate (in the direction of the rotational force). Given that each of the first and second threaded portions of the threaded shaft 206 are threaded in opposing direction, the rotation of the shaft 202 causes the respective translator elements 210A, 210B to move along the longitudinal direction of the shaft 202 in opposite directions. In the illustrated embodiment, simultaneous deployment of the anchoring elements 120 takes place as the respective translator elements 210A, 210B move away from one another. In an alternative embodiment, each anchoring element 120 may be disposed on an opposite side of the respective translator element 210 (with corresponding changes in the orientation of the respective aperture 122) such that deployment of the of the anchoring elements 120 takes place as the respective translator elements 210A, 210B move toward one another.

It is noted that any of the devices 100, 100A, 100B, 100C discussed above may include one or more of the particular features of each device (where conflicts would not occur) in order to achieve the resultant functionality of such feature as would be readily apparent to the skilled artisan. Indeed, for example the device 100C shows the anchoring elements 120 all in the same general plane (i.e., a laterally extending plane with respect to the geometry of the body of the device). However, modifications to achieve additional variation in the deployment trajectories of the anchoring elements 120 may be achieved by taking certain of the structure and function from other embodiments, and vice versa. Alternatively, or additionally, the deployment of the respective anchoring elements 120 may be achieved using the instrument 250 of FIG. 6, assuming that the shaft 202 is not employed.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method of inserting an intervertebral prosthesis into an intervertebral space between respective endplates of adjacent first and second vertebral bones of a spine, comprising:
   placing the intervertebral prosthesis into the intervertebral space, the intervertebral prosthesis including: a body including first and second spaced apart major surfaces and at least one sidewall extending therebetween, the first major surface for engaging the endplate of the first vertebral bone, and the second major surface for engaging the endplate of the second vertebral bone, and the first and second major surfaces defining a longitudinal axis extending substantially normal to said surfaces; and
   simultaneously pushing at least three anchoring elements from within the body of the intervertebral prosthesis out through at least three respective apertures in the body and into at least one of the first and second vertebral bones, without rotating the at least three anchoring elements about respective axes thereof, wherein:
   a first deployment direction of a first of the anchoring elements includes: (i) a first substantial directional component in one of an anterior and posterior direction of the body; and (ii) a second substantial directional component parallel to the longitudinal axis of the body;
   a second deployment direction of a second of the anchoring elements includes: (i) a first substantial directional component in one of an anterior and posterior direction of the body; and (ii) a second substantial directional component parallel to the longitudinal axis of the body and opposite to the second substantial directional component of the first deployment direction of the first anchoring element; and
   the step of pushing the at least three anchoring elements from within the body of the intervertebral prosthesis out through at least three respective apertures and into the at least one of the first and second vertebral bones, includes moving the first anchoring element at least some distance in the first deployment direction and moving the second anchoring element at least some distance in the second deployment direction.

2. The method of claim 1, wherein directions of deployment of the anchoring elements are transverse to the longitudinal axis of the body.

3. The method of claim 1, wherein:
   a third deployment direction of a third of the anchoring elements includes: (i) a first substantial directional component in one of an anterior and posterior direction of the body; (ii) a second substantial directional component parallel to the longitudinal axis of the body; and (iii) a third substantial directional component in a lateral direction with respect to the anterior-posterior direction of the body;

at least one of the first and second substantial directional components of the third deployment direction are substantially opposite to the respective first and second substantial directional components of at least one of the first and second deployment directions; and the step of pushing the at least three anchoring elements from within the body of the intervertebral prosthesis out through at least three respective apertures and into the at least one of the first and second vertebral bones, further includes moving the third anchoring element at least some distance in the third deployment direction.

4. The method of claim 3, wherein:

a fourth deployment direction of a fourth of the anchoring elements includes: (i) a first substantial directional component in one of an anterior and posterior direction of the body; (ii) a second substantial directional component parallel to the longitudinal axis of the body; and (iii) a third substantial directional component in a lateral direction with respect to the anterior-posterior direction of the body;

at least two of the first, second, and third substantial directional components of the fourth deployment direction are substantially opposite to at least one of: (i) the respective first and second substantial directional components of at least one of the first and second deployment directions, and (ii) the respective first, second, and third substantial directional components of the third deployment direction; and the step of pushing the at least three anchoring elements from within the body of the intervertebral prosthesis out through at least three respective apertures and into the at least one of the first and second vertebral bones, further includes moving the fourth anchoring element at least some distance in the fourth deployment direction.

5. A method of inserting an intervertebral prosthesis into an intervertebral space between respective endplates of adjacent first and second vertebral bones of a spine, comprising:

placing the intervertebral prosthesis into the intervertebral space, the intervertebral prosthesis including: (i) a body including first and second spaced apart major surfaces and at least one sidewall extending therebetween, the first major surface for engaging the endplate of the first vertebral bone, and the second major surface for engaging the endplate of the second vertebral bone, and the first and second major surfaces defining a longitudinal axis extending substantially normal to said surfaces, (ii) at least three apertures extending from within the body and each aperture opening at one of the first and second major surfaces, (iii) at least three anchoring elements, each anchoring element disposed within a respective one of the at least three apertures and including a shaft having proximal and distal ends, and (iv) a drive mechanism engaging the proximal end of each anchoring element and the drive mechanism having a head at a proximal end of a single threaded shaft extending therefrom, thereby defining a longitudinal axis thereof; and a translator element having: (a) a threaded bore in threaded engagement with the threaded shaft of the drive shaft, (b) at least one coupling element in engagement with, and permitting articulation of, the proximal end of each anchoring element, wherein the drive shaft is fixed in a direction of the longitudinal axis thereof, but rotatable, within the body, such that a rotation force on the drive shaft causes the translator to: (a) move along the longitudinal axis of the drive shaft, (b) translate each of the proximal ends of the at least three anchoring elements parallel to the longitudinal axis of the drive shaft, and (c) push the at least three anchoring elements out through the respective apertures; and activating the drive mechanism in order to simultaneously push the at least three anchoring elements from within the body of the intervertebral prosthesis out through at least three respective apertures in the body and into at least one of the first and second vertebral bones, without rotating any of the at least three anchoring elements about respective axes thereof.

6. The method of claim 5, wherein at least one of:

a first deployment direction of a first of the anchoring elements includes: (i) a first substantial directional component in one of a first lateral direction of the body and a second, opposing, lateral direction of the body; and (ii) a second substantial directional component parallel to the longitudinal axis of the body;

a second deployment direction of a second of the anchoring elements includes: (i) a first substantial directional component in one of the first lateral direction of the body and the second, opposing, lateral direction of the body; and (ii) a second substantial directional component parallel to the longitudinal axis of the body and opposite to the second substantial directional component of the first deployment direction of the first anchoring element.

7. The method of claim 6, wherein:

a third deployment direction of a third of the anchoring elements includes: (i) a first substantial directional component in one of the first lateral direction of the body and the second, opposing, lateral direction of the body; and (ii) a second substantial directional component parallel to the longitudinal axis of the body; and at least one of the first and second substantial directional components of the third deployment direction is substantially opposite to the respective first and second substantial directional components of at least one of the first and second deployment directions.

8. The method of claim 7, wherein:

a fourth deployment direction of a fourth of the anchoring elements includes: (i) a first substantial directional component in one of the first lateral direction of the body and the second, opposing, lateral direction of the body; and (ii) a second substantial directional component parallel to the longitudinal axis of the body; and at least one of the first and second substantial directional components of the fourth deployment direction is substantially opposite to the respective first and second substantial directional components of at least two of the first, second, and third deployment directions.

9. The method of claim 5, wherein:

a first deployment direction of a first of the anchoring elements includes: (i) a first substantial directional component in one of an anterior and posterior direction of the body; and (ii) a second substantial directional component parallel to the longitudinal axis of the body;

a second deployment direction of a second of the anchoring elements includes: (i) a first substantial directional component in one of an anterior and posterior direction of the body; and (ii) a second substantial directional component parallel to the longitudinal axis of the body and opposite to the second substantial directional component of the first deployment direction of the first anchoring element; and the step of pushing the at least three anchoring elements from within the body of the intervertebral prosthesis out through at least three respective apertures and into the at least one of the first and second vertebral bones, includes moving the first anchoring element at least some distance in the first deployment direction and moving the second anchoring element at least some distance in the second deployment direction.

10. The method of claim 9, wherein:
a third deployment direction of a third of the anchoring elements includes: (i) a first substantial directional component in one of an anterior and posterior direction of the body; (ii) a second substantial directional component parallel to the longitudinal axis of the body; and (iii) a third substantial directional component in a lateral direction with respect to the anterior-posterior direction of the body;
at least one of the first and second substantial directional components of the third deployment direction are substantially opposite to the respective first and second substantial directional components of at least one of the first and second deployment directions; and
the step of pushing the at least three anchoring elements from within the body of the intervertebral prosthesis out through at least three respective apertures and into the at least one of the first and second vertebral bones, further includes moving the third anchoring element at least some distance in the third deployment direction.

11. The method of claim 10, wherein:
a fourth deployment direction of a fourth of the anchoring elements includes: (i) a first substantial directional component in one of an anterior and posterior direction of the body; (ii) a second substantial directional component parallel to the longitudinal axis of the body; and (iii) a third substantial directional component in a lateral direction with respect to the anterior-posterior direction of the body;
at least two of the first, second, and third substantial directional components of the fourth deployment direction are substantially opposite to at least one of: (i) the respective first and second substantial directional components of at least one of the first and second deployment directions, and (ii) the respective first, second, and third substantial directional components of the third deployment direction; and
the step of pushing the at least three anchoring elements from within the body of the intervertebral prosthesis out through at least three respective apertures and into the at least one of the first and second vertebral bones, further includes moving the fourth anchoring element at least some distance in the fourth deployment direction.

* * * * *